(12) United States Patent
Nagane et al.

(10) Patent No.: US 9,562,004 B2
(45) Date of Patent: Feb. 7, 2017

(54) 2, 2'-BIS (4-HYDROXYPHENYL) ALKYL AZIDES AND PROCESS FOR THE PREPARATION THEREOF

(71) Applicant: COUNCIL OF SCIENTIFIC & INDUSTRIAL RESEARCH, New Delhi (IN)

(72) Inventors: Samadhan Suresh Nagane, Maharashtra (IN); Prakash Sudhir Sane, Maharashtra (IN); Bhausaheb Vilas Tawade, Maharashtra (IN); Prakash Purushottam Wadgaonkar, Maharashtra (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 55 days.

(21) Appl. No.: 14/441,469

(22) PCT Filed: Nov. 7, 2013

(86) PCT No.: PCT/IN2013/000685
§ 371 (c)(1),
(2) Date: May 7, 2015

(87) PCT Pub. No.: WO2014/073001
PCT Pub. Date: May 15, 2014

(65) Prior Publication Data
US 2015/0274646 A1 Oct. 1, 2015

(30) Foreign Application Priority Data
Nov. 7, 2012 (IN) .......................... 3439/DEL/2012

(51) Int. Cl.
*C07C 247/10* (2006.01)
*C08G 63/685* (2006.01)
*C08G 63/91* (2006.01)

(52) U.S. Cl.
CPC ......... *C07C 247/10* (2013.01); *C08G 63/6856* (2013.01); *C08G 63/916* (2013.01)

(58) Field of Classification Search
CPC ............................ C07C 247/06; C07C 247/10
(Continued)

(56) References Cited

U.S. PATENT DOCUMENTS

| 4,162,247 A * | 7/1979 | Mayer ................... C07C 243/32 |
| | | 252/404 |
| H000428 H * | 2/1988 | Gilbert .................. C07C 247/10 |
| | | 149/122 |

(Continued)

FOREIGN PATENT DOCUMENTS

EP 0839798 A2 * 5/1998 ............. C07C 33/46
WO WO 2005/004795 1/2005

OTHER PUBLICATIONS

Prakash S. Sane, et al.: "Aromatic aldehyde functionalized polycaprolactone and polystyrene macromonomers: Synthesis, characterization and aldehyde-aminooxy click reaction". Reactive & Function Polymers., vol. 72, No. 10, Jul. 6, 2012 (Jul. 6, 2012), pp. 713-721, the whole document.

(Continued)

*Primary Examiner* — Mike M Dollinger
(74) *Attorney, Agent, or Firm* — Workman Nydegger

(57) ABSTRACT

The application discloses monomers based on bisphenols with pendent reactive azido groups. The application further provides a process for preparation of bisphenol monomers with pendent reactive azido groups which are used further for preparing polymers with pendent reactive functional groups and graft copolymer.

12 Claims, 3 Drawing Sheets

(58) Field of Classification Search
USPC .......................................................... 525/534
See application file for complete search history.

(56) References Cited

U.S. PATENT DOCUMENTS

| | | | | |
|---|---|---|---|---|
| 5,391,772 | A * | 2/1995 | Thompson | C07C 247/06 540/557 |
| 5,475,065 | A * | 12/1995 | Guiver | C08G 75/23 525/535 |
| 7,446,234 | B2 * | 11/2008 | More | C07C 37/20 568/718 |
| 2007/0191606 | A1 | 8/2007 | Mallikarjuna et al. | |
| 2014/0058058 | A1 * | 2/2014 | Song | A61L 27/18 528/271 |
| 2014/0088048 | A1 * | 3/2014 | Ali | C07C 291/08 514/150 |

OTHER PUBLICATIONS

PCT/IN2013/000685, Feb. 14, 2014, International Search Report and Written Opinion.

* cited by examiner

2,2'-BIS (4-HYDROXYPHENYL) ALKYL AZIDES AND PROCESS FOR THE PREPARATION THEREOF

FIELD OF THE INVENTION

The invention relates to novel bisphenol monomers containing pendent azido groups and process for preparation thereof. Further the invention relates to novel polymers containing pendent azido groups prepared from bisphenol monomers of the present investigation.

BACKGROUND AND PRIOR ART OF THE INVENTION

Polymers synthesized by step growth polymerizations find notable applications in textiles, the automobile industry, coatings and so on. The industrial applications mainly depend on the chemical nature of the starting components and on the industrial process. Nevertheless, for more specific applications, many of these polymers are limited in scope because of the lack of functionalities on the backbone for further modification and tailoring.

Bisphenols are an important class of difunctional monomers which find applications in the preparation of a host of high performance polymers such as polycarbonates, polyesters, polyether sulfones, polyether ether ketones, epoxy resins, etc. US Patent Application Publication No. 20070191606 discloses novel 2,2-bis(4-hydroxyphenyl) alkylonium salts of formula (1):

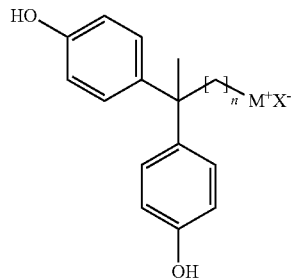

wherein n=1 to 37, X=Cl, Br, $BF_4$, OTf, or $NTf_2$, M=trialkylphosphonium, triarylphosphonium, triaryl-alkylphosphonium, ammonium or substituted cylic amidinium radical selected from the group containing pyrrole, imidazole, thiazole, oxazole, pyridine, pyrimidine, quinoline, isoquiniline, indole, purine, benzimidazole, benzothiaozole, benzoxazole, pyrazine, quinoxaline, quinozoline, acridine, phenazine, imidazopyridine and dipyridyl.

It is believed that the potential applications of polymers could be greatly broadened with the incorporation of pendent groups onto the polymer backbone. Towards this end, difunctional monomers containing pendent reactive groups which are compatible under polymerization conditions are highly desirable. The introduction of pendent reactive functional groups into these polymers via utilization of bisphenols containing appropriate functional groups is of great interest as pendent functional groups offer the possibility of synthesis of graft copolymers comprising polycondensate and polyvinyl segments. Such graft copolymers are potentially useful as blend compatibilizers and so on.

Therefore there is a need in the art to provide more monomers based on bisphenols with pendent reactive functional groups, so that these can afford preparation of high performance polymers.

OBJECTS OF THE INVENTION

The main objective of the present invention is to provide bisphenol monomers with pendent azido functional groups.

Another objective of the invention is to provide a process of synthesis for novel bisphenol monomers with pendent azido functional groups.

One more objective of the invention is to provide polymers based on novel bisphenol monomers with pendent azido functional groups.

SUMMARY OF THE INVENTION

Accordingly, the present invention provides a Novel bis (4-hydroxyphenyl)alkyl azide compounds of Formula I,

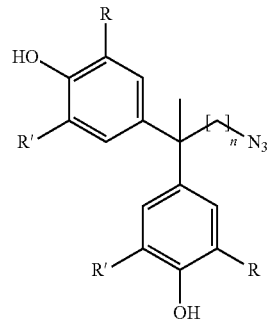

Formula I

Bis(4-hydroxyphenyl) alkyl azides
R and R' = —H, alkyl (linear or branched), —Cl, —Br, $NO_2$.
n = 1-36.

In an embodiment of the present invention, wherein said compound is 4,4'-(5-azidoalkane-2,2-diyl)diphenol for formula II.

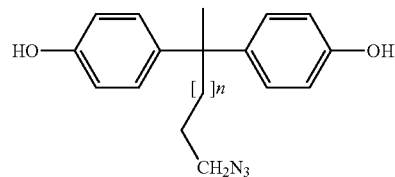

Formula II

In an embodiment of the present invention, wherein said compound is 4,4'-(5-azidopentane-2,2-diyl)diphenol for formula III.

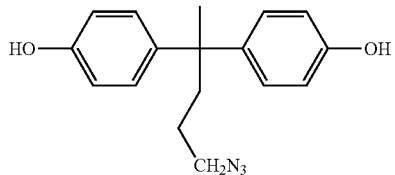

Formula III

In another embodiment of the present invention, the monomers of the present invention contain pendent reactive azido groups, which could be further exploited in chemical modifications of polymers derived therefrom using a 'click chemistry' approach.

The present invention further provides a process for preparing 4,4'-(5-azidoalkane-2,2-diyl)diphenol of Formula II, said process comprising:
(a) esterification of 4,4'-bis(4-hydroxyphenyl)alkanoic acid using methanol in the presence of concentrated sulphuric acid catalyst and purifying product of reaction to obtain alkyl 4,4'-bis(4-hydroxyphenyl)alkanoate;
(b) reduction of alkyl 4,4'-bis(4-hydroxyphenyl)alkanoate of step (a) using lithium aluminium hydride to obtain 4,4'-(5-hydroxyalkane-2,2-diyl)diphenol;
(c) bromination of 4,4'-(5-hydroxyalkane-2,2-diyl)diphenol of step (b) using carbon tertabromide and triphenyl phosphine to obtain 4,4'-(5-bromoalkane-2,2-diyl)diphenol; and
(d) substitution of bromo group in 4,4'-(5-bromoalkane-2,2-diyl)diphenol of step (c) using sodium azide in a solvent to obtain 4,4'-(5-azidoalkane-2,2-diyl)diphenol.

In an embodiment of the present invention, the solvent used in step (d) of said process is selected from DMSO, DMF, DMAc and acetonitrile.

The present invention also provides a process for the synthesis of polyesters or copolyesters of the compound of formula I, wherein said process is selected from interfacial polycondensation and solution polycondensation.

In an embodiment of the present invention, wherein said interfacial polycondensation process comprises:
a. dissolving 4,4'-(5-azidoalkane-2,2-diyl)diphenol in an alkali solution and stirring the mixture to obtain the reaction mixture;
b. adding benzyl triethyl ammonium chloride to the reaction mixture of step (a) and stirring followed by addition of a solution of diacid chloride in dichloromethane to the reaction mixture and stirring vigorously; and
c. pouring the reaction mixture of step (b) into hot water; filtering the precipitated polymer and washing it several times with water followed by work-up to obtain the desired product.

In an embodiment of the present invention, wherein said diacid chloride is selected from terephthaloyl chloride, isophthaloyl chloride and mixtures thereof.

In an embodiment of the present invention, wherein said solution polycondensation process comprises:
a. cooling a solution of 4,4'-(5-azidoalkane-2,2-diyl)diphenol to 0° C.;
b. adding a solution of diacid chloride drop wise with stirring to obtain a solution and
c. pouring the solution of step b into hexane to obtain the desired product.

In an embodiment of the present invention, wherein said diacid chloride is selected from terephthaloyl chloride, isophthaloyl chloride and mixtures thereof.

The present invention also provides a process for the synthesis of modified polymers or graft copolymers from the polymer synthesized from the compound of Formula I by reacting with alkynes, substituted alkynes or polymers terminated with alkynes, said process comprising: reacting the polymers based on the compound of Formula I with alkynes, substituted alkynes or polymer terminated with alkynes in a sealed, inert atmosphere and working up to obtain the desired product.

The invention discloses bisphenol monomers with pendent azido functional groups. The invention further provides a process for preparation of bisphenol monomers with pendent azido functional groups. The novel bisphenols with pendent reactive functional groups are used for providing polymers with pendent azido functional groups.

BRIEF DESCRIPTION OF FIGURES

In the figures accompanying the specification.

DETAILED DESCRIPTION OF THE INVENTION

Figure 1:
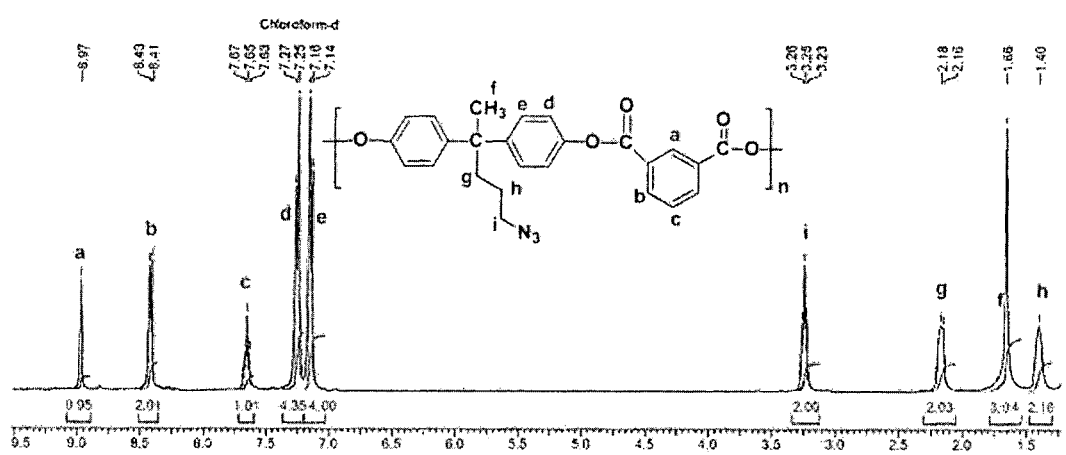
FIG. 1 illustrates $^1$H-NMR spectrum of polyester obtained by polycondensation of 4,4'-(5-azidopentane-2,2-diyl)diphenol and isophthaloyl chloride.

The invention will now be described in detail in connection with certain preferred and optional embodiments, so that various aspects thereof may be more fully understood and appreciated.

Accordingly, the invention discloses the compound of formula I, bis(4-hydroxyphenyl)alkyl azides,

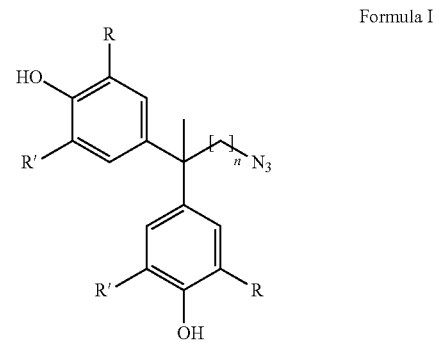

Formula I

Bis(4-hydroxyphenyl) alkyl azides
R and R' = —H, alkyl (linear or branched), —Cl, —Br, NO$_2$.
n = 1-36.

In an embodiment of the present invention, wherein said compound is 4,4'-(5-azidoalkane-2,2-diyl)diphenol for formula II.

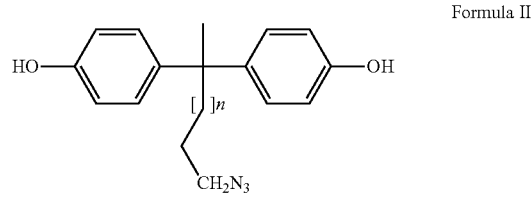

Formula II

In a preferred embodiment, the compound of formula I is 4,4'-(5-azidopentane-2,2-diyl)diphenol (shown below as Formula III).

Formula III

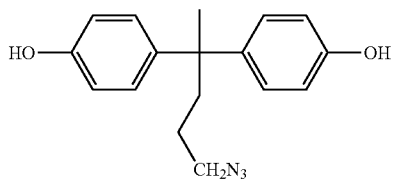

The present invention further provides a process for preparing 4,4'-(5-azidoalkane-2,2-diyl)diphenol of Formula II, said process comprising:

(e) esterification of 4,4'-bis(4-hydroxyphenyl)alkanoic acid using methanol in the presence of a concentrated sulphuric acid catalyst and purifying product of reaction to obtain alkyl 4,4'-bis(4-hydroxyphenyl)alkanoate;

(f) reduction of alkyl 4,4'-bis(4-hydroxyphenyl)alkanoate of step (a) using lithium aluminium hydride to obtain 4,4'-(5-hydroxyalkane-2,2-diyl)diphenol;

(g) bromination of 4,4'-(5-hydroxyalkane-2,2-diyl)diphenol of step (b) using carbon tertabromide and triphenyl phosphine to obtain 4,4'-(5-bromoalkane-2,2-diyl)diphenol; and (h) substitution of bromo group in 4,4'-(5-bromoalkane-2,2-diyl)diphenol of step (c) using sodium azide in a solvent to obtain 4,4'-(5-azidoalkane-2,2-diyl)diphenol.

A schematic representation of the aforesaid process is provided herein below:

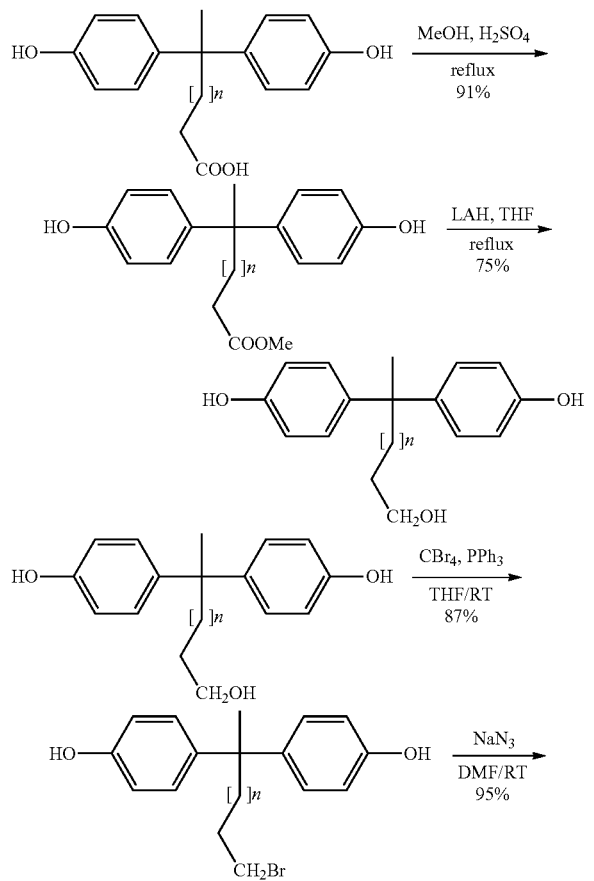

Other compounds of the general Formula I (i.e. bis(4-hydroxyphenyl)alkyl azides) having different substitutions may be prepared by the process as disclosed above.

In particular, the present invention provides a process for preparing the compound of formula III comprising the steps of:

1. esterification of 4,4'-bis(4-hydroxyphenyl)pentanoic acid using methanol in the presence of an acid catalyst and purifying product of reaction to obtain methyl 4,4'-bis(4-hydroxyphenyl)pentanoate;

2. reduction of methyl 4,4'-bis(4-hydroxyphenyl)pentanoate using lithium aluminium hydride to obtain 4,4'-(5-hydroxypentane-2,2-diyl)diphenol;

3. bromination of 4,4'-(5-hydroxypentane-2,2-diyl)diphenol using carbon tertabromide and triphenyl phosphine to obtain 4,4'-(5-bromopentane-2,2-diyl)diphenol and 4. substitution of bromo group in 4,4'-(5-bromopentane-2,2-diyl)diphenol using sodium azide in a solvent to obtain 4,4'-(5-azidopentane-2,2-diyl)diphenol.

The solvents in step 4 are selected from DMSO, DMF, DMAc, acetonitrile and such like while the reaction temperature of step 4 may be varied from room temperature to 80° C.

A schematic representation of the aforesaid process is provided herein below:

Scheme: Synthesis of 4,4'-(5-azidopentane-2,2-diyl) diphenol

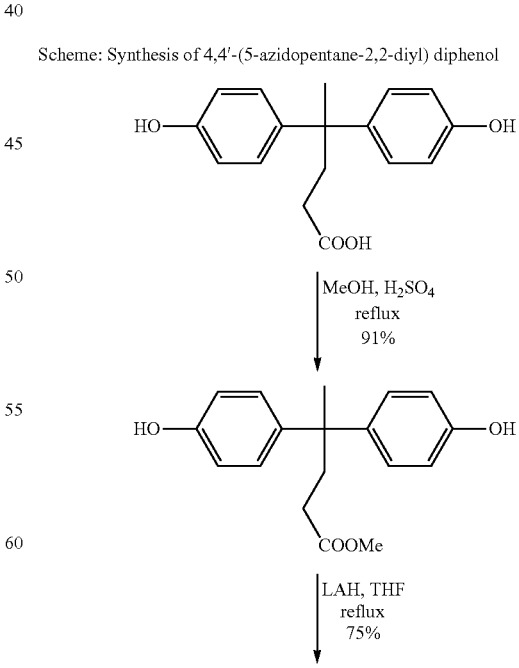

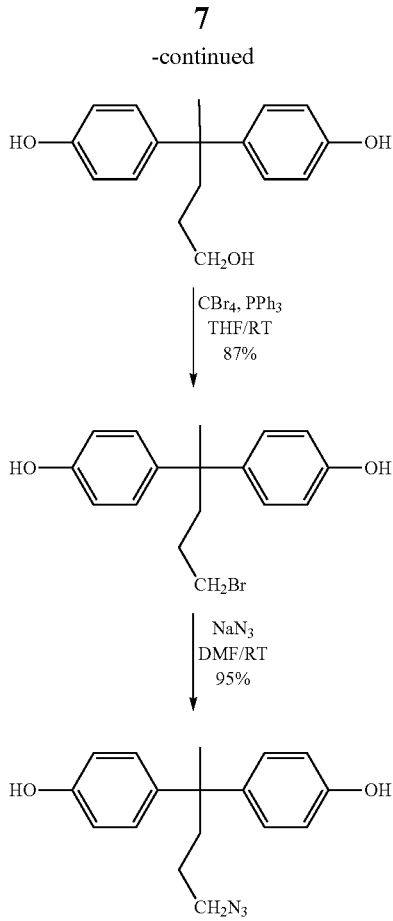

In an embodiment of the invention, the novel bisphenol monomers with pendant reactive functional groups are used for the preparation of polymers with pendant functional groups.

In an embodiment of the invention, a series of novel polyesters or co polyesters are synthesized by interfacial polycondensation or solution polycondensation of 4,4'-(5-azidopentane-2,2-diyl)diphenol with aromatic diacid chlorides or mixtures thereof, selected from, but not limited to terephthaloyl chloride and isophthaloyl chloride.

In a preferred embodiment of the invention, polyester or copolyester was synthesized from 4,4'-(5-azidopentane-2,2-diyl)diphenol.

In the polymerization reaction, 4,4'-(5-azidopentane-2,2-diyl)diphenol was dissolved in an alkali solution. The mixture was stirred for 1 hr at 10° C. Next, benzyl triethyl ammonium chloride was added to the reaction mixture and stirring was continued. After some time, a solution of isophthaloyl chloride in dichloromethane was added to the reaction mixture and the mixture was stirred vigorously at 2000 rpm for 1 h. The reaction mixture was poured into hot water; the precipitated polymer was filtered and washed several times with water. The polymer was dissolved in chloroform and reprecipitated into methanol. The polymer was filtered, washed with methanol, and dried under reduced pressure at 50° C. for 24 h.

In another preferred embodiment, polyester or copolyester was synthesized from 4,4'-(5-azidopentane-2,2-diyl)diphenol by a process of solution polycondensation comprising:
a. cooling a solution of 4,4'-(5-azidopentane-2,2-diyl) diphenol to 0° C.;
b. adding a solution of diacid chloride drop wise with stirring to obtain a solution; and
c. pouring the solution of step b into hexane to obtain the desired product.

In an embodiment, said diacid chloride is selected from terephthaloyl chloride, isophthaloyl chloride and mixtures thereof.

In an aspect, the polymer synthesized from the compound of Formula I was reacted with alkynes, substituted alkynes or polymers terminated with alkynes to obtain modified polymers or graft copolymers, said process comprising: reacting the polymers based on the compound of Formula I with alkynes, substituted alkynes or polymer terminated with alkynes in a sealed, inert atmosphere and working up to obtain the desired product.

New bisphenols containing pendent azido groups were synthesized which when incorporated into polymers result in polymers containing reactive azido groups. The presence of pendent azido groups provides reactive sites for post-functionalization by reaction with functionalized alkynes or alkyne-terminated low molecular weight polymers affording polymers containing pendant reactive groups and graft copolymers, respectively.

The invention will now be described in detail in connection with certain preferred and optional embodiments, so that various aspects thereof may be more fully understood and appreciated.

The following examples are given by way of illustrations and should not be construed to limit the scope of the present invention.

EXAMPLES

Example 1

A. Synthesis of methyl 4,4'-bis(4-hydroxyphenyl)pentanoate

Into a 500 mL two necked round-bottom flask equipped with a reflux condenser were charged, 4,4'-bis(4-hydroxyphenyl)pentanoic acid (25 g, 87.32 mmol), and methanol (300 mL). The reaction mixture was stirred for 15 minutes, followed by addition of concentrated sulphuric acid (1.5 mL). The reaction mixture was refluxed for 8 h. Methanol was removed under reduced pressure and ethyl acetate (300 mL) was added to the reaction mixture. The ethyl acetate solution was washed with saturated brine solution (3×50 mL) and dried over anhydrous sodium sulfate, filtered and evaporated under reduced pressure. The crude product was purified by column chromatography using ethyl acetate:pet ether (50:50, v/v) as eluent to afford 23.8 g (90.85%) of methyl 4,4'-bis(4-hydroxyphenyl)pentanoate.

IR (CHCl$_3$, cm$^{-1}$): 1730

$^1$H NMR (DMSO-d$_6$ δ/ppm): 9.24 (s, 2H, phenolic OH), 6.97 (d, 4H, Ar—H meta to phenolic OH), 6.69 (d, 4H, Ar—H ortho to phenolic OH), 3.53 (s, 3H, OCH$_3$), 2.31-2.23 (m, 2H, —CH$_2$—CH$_2$), 2.08-2.01 (m, 2H, —CH$_2$—CH$_2$), 1.47 (s, 3H, —CH$_3$).

B. Synthesis of 4,4'-(5-hydroxypentane-2,2-diyl)diphenol

Into a 250 mL two necked round-bottom flask equipped with a dropping funnel were charged, lithium aluminium hydride (1.85 g, 48.99 mmol) and dry THF (80 mL). The solution of methyl 4,4'-bis(4-hydroxyphenyl)pentanoate (16.2 g, 54 mmol) in dry THF (30 mL) was added over a period of 30 minutes. Effervescences were observed during the addition. Reaction mixture was stirred for 8 h, cooled and then moist sodium sulfate was added to deactivate Lithium aluminium hydride. Dilute HCl (10 mL) was added to dissolve the formed salt and ethyl acetate (150 mL) was added. The ethyl acetate solution was washed with saturated brine solution (3×30 mL), sodium bicarbonate solution (3×30 mL), and water (2×50 mL). The ethyl acetate layer was separated, dried over sodium sulfate, filtered and solvent was evaporated under reduced pressure. The crude product was purified by column chromatography using ethyl acetate:pet ether (40:60, v/v) to afford 3.4 g (75%) of 4,4'-(5-hydroxypentane-2,2-diyl)diphenol as a white powder.

IR (CHCl$_3$, cm$^{-1}$): 3150

$^1$H NMR (Acetone-d$_6$, δ/ppm): 8.28 (s, 2H, phenolic OH), 7.05 (d, 4H, Ar—H meta to phenolic OH), 6.75 (d, 4H, Ar—H ortho to phenolic OH), 3.53 (t, 2H, —CH$_2$OH), 2.10-2.06 (m, 2H, —CH$_2$), 1.56 (s, 3H, —CH$_3$), 1.39-1.31 (m, 2H, —CH$_2$)

C. Synthesis of 4,4'-(5-bromopentane-2,2-diyl)diphenol

Into a 250 mL two necked round-bottom flask were taken 4,4'-(5-hydroxypentane-2,2-diyl)diphenol (5 g, 18.38 mmol) and dry THF (60 mL) and the solution was cooled to 0° C. To the reaction mixture were added carbon tetrabromide (7.3 g, 22.05 mmol) and triphenyl phosphine (5.78 g, 22.05 mmol) dissolved in tetrahydrofuran dropwise and the reaction mixture was stirred for 2 h at room temperature. THF was evaporated under reduced pressure and the reaction mixture was washed with water (2×50 ml) and extracted into dichloromethane. The dichloromethane solution was washed with saturated brine solution (3×50 mL) and dried over anhydrous sodium sulfate, filtered and evaporated under reduced pressure. The crude product was purified by column chromatography using ethyl acetate:pet ether (15:85, v/v) to afford 5.4 g (87.70%) of 4,4'-(5-bromopentane-2,2-diyl) diphenol as a pale yellow oily liquid.

$^1$H NMR (CDCl3, δ/ppm): 6.03 (s, 2H, phenolic OH), 7.05 (d, 4H, Ar—H meta to phenolic OH), 6.75 (d, 4H, Ar—H ortho to phenolic OH), 3.36 (t, 2H, —CH$_2$Br), 2.17 (m, 2H, —CH$_2$), 1.58 (s, 3H, —CH$_3$), 1.66 (m, 2H, —CH$_2$)

D. Synthesis of 4,4'-(5-azidopentane-2,2-diyl)diphenol

Into a 250 mL single necked round-bottom flask were taken 4,4'-(5-bromopentane-2,2-diyl)diphenol (5 g, 14.92 mmol) and N,N-dimethylformamide (60 ml). Sodium azide (4.85 g, 74.62 mmol) was added to the solution and the reaction mixture was stirred for 24 h at room temperature. The reaction mixture was washed with water and was extracted with ethyl acetate (2 times). The ethyl acetate solution was washed with saturated brine solution (3×50 mL) and dried over anhydrous sodium sulfate, filtered and evaporated under reduced pressure. The crude product was purified by column chromatography using ethyl acetate:pet ether (30:70, v/v) to afford 4.2 g (95%) of 4,4'-(5-azidopentane-2,2-diyl)diphenol as a pale yellow oily liquid.

IR: 2097 cm$^{-1}$ $^1$H NMR (CDCl3, δ/ppm): 6.38 (s, 2H, phenolic OH), 7.05 (d, 4H, Ar—H meta to phenolic OH), 6.75 (d, 4H, Ar—H ortho to phenolic OH), 3.24 (t, 2H, —CH$_2$N$_3$), 2.11 (m, 2H, —CH$_2$), 1.58 (s, 3H, —CH$_3$), 1.41 (m, 2H, —CH$_2$)

Example 2

Synthesis of polyester by polycondensation of 4,4'-(5-azidopentane-2,2-diyl)diphenol and isophthaloyl chloride Into a 100 mL two-necked round bottom flask equipped with a mechanical stirrer, 4,4'-(5-azidopentane-2,2-diyl)diphenol (1 g, 3.35 mmol) was dissolved in 10 mL of 10 mmol solution of sodium hydroxide. The mixture was stirred for 1 h at 10° C. Next, benzyl triethyl ammonium chloride (30 mg) was added to the reaction mixture and stirring was continued. After 30 min, a solution of isophthaloyl chloride (0.680 g, 3.35 mmol) in 20 mL of dichloromethane was added to the reaction mixture and the mixture was stirred vigorously at 2000 rpm for 1 h. The reaction mixture was poured into hot water; the precipitated polymer was filtered and washed several times with water. The polymer was dissolved in chloroform and reprecipitated into methanol. The polymer was filtered, washed with methanol, and dried under reduced pressure at 50° C. for 24 h.

Inherent viscosity—1.38 dL/g

Molecular Weight: Mn=91,200 g/mol (GPC in Chloroform, Polystyrene standard), IR-2099 cm$^{-1}$ NMR—$^1$H-NMR spectrum of polyester of 4,4'-(5-azidopentane-2,2-diyl)diphenol and isophthaloyl chloride is shown in FIG. 1.

Example 3

Synthesis of polyester by polycondensation of 4,4'-(5-azidopentane-2,2-diyl)diphenol and terephthaloyl chloride Into a 100 mL two-necked round bottom flask equipped with a mechanical stirrer, 4,4'-(5-Azidopentane-2,2-diyl) diphenol (1 g, 3.35 mmol) was dissolved in 10 mL of 10 mmol solution of sodium hydroxide. The mixture was stirred for 1 h at 10° C. Next, benzyl triethyl ammonium chloride (30 mg) was added to the reaction mixture and stirring was continued. After 30 min, a solution of terephthaloyl chloride (0.680 g, 3.35 mmol) in 20 mL of dichloromethane was added to the reaction mixture and the mixture was stirred vigorously at 2000 rpm for 1 h. The reaction mixture was poured into hot water; the precipitated polymer was filtered and washed several times with water. The polymer was dissolved in chloroform and reprecipitated into methanol. The polymer was filtered, washed with methanol, and dried under reduced pressure at 50° C. for 24 h.

Inherent viscosity—1.25 dL/g.

Molecular Weight: Mn=1,17,100 g/mol (GPC in Chloroform, Polystyrene standard), IR-2099 cm$^{-1}$ Example 4

Synthesis of copolyester by polycondensation of 4,4'-(5-azidopentane-2,2-diyl)diphenol, with mixture of isophthaloyl chloride and terephthaloyl chloride Into a 100 mL two-necked round bottom flask equipped with a mechanical stirrer, 4,4'-(5-Azidopentane-2,2-diyl) diphenol (1 g, 3.35 mmol) was dissolved in 10 mL of 10 mmol solution of sodium hydroxide. The mixture was stirred for 1 h at 10° C. Next, benzyl triethyl ammonium chloride (30 mg) was added to the reaction mixture and stirring was continued. After 30 min, a solution of isophthaloyl chloride (0.340 g, 1.675 mmol) and terephthaloyl chloride (0.340 g, 1.675 mmol) in 20 mL of dichloromethane was added to the reaction mixture and the mixture was stirred vigorously at 2000 rpm for 1 h. The reaction mixture was poured into hot water; the precipitated polymer was filtered and washed several times with water. The polymer was dissolved in chloroform and reprecipitated into methanol. The polymer was filtered, washed with methanol, and dried under reduced pressure at 50° C. for 24 h.

Inherent viscosity—1.0 dL/g

Molecular Weight: Mn=75,200 g/mol (GPC in Chloroform, Polystyrene standard), IR-2099 cm$^{-1}$

Example 5

Synthesis of copolyester by polycondensation of 4,4'-(5-azidopentane-2,2-diyl)diphenol and 4,4'-(1-phenylethane-1,1-diyl)diphenol with isophthaloyl chloride Into a 100 mL two-necked round bottom flask equipped with a high-speed mechanical stirrer and an addition funnel were placed 4,4'-(5-azidopentane-2,2-diyl)diphenol (0.5 g, 1.683×10-3 mol), 4,4'-(1-phenylethane-1,1-diyl)diphenol (1.162 g, 3.927×10-3 mol) dissolved in 1M NaOH (12 mL). The reaction mixture was stirred at 10° C. for 1 h. Thereafter, BTEAC (77 mg) was added to the reaction mixture. The solution of isophthaloyl chloride (1.138 g, 5.61×10-3 mol) dissolved in dichloromethane (20 mL) was added in one lot to the reaction mixture and was stirred vigorously at 2000 rpm at 10° C. for 1 h. The reaction mixture was poured into hot water; the precipitated polymer was filtered and washed several times with water. Polymer was dissolved in dichloromethane (20 mL) and precipitated into methanol:water (1:1, v/v) mixture (1000 mL). Polymer was filtered, washed with methanol and dried at 50° C. under reduced pressure for two days.

Inherent viscosity— 0.73 dL/g

Figure 2:
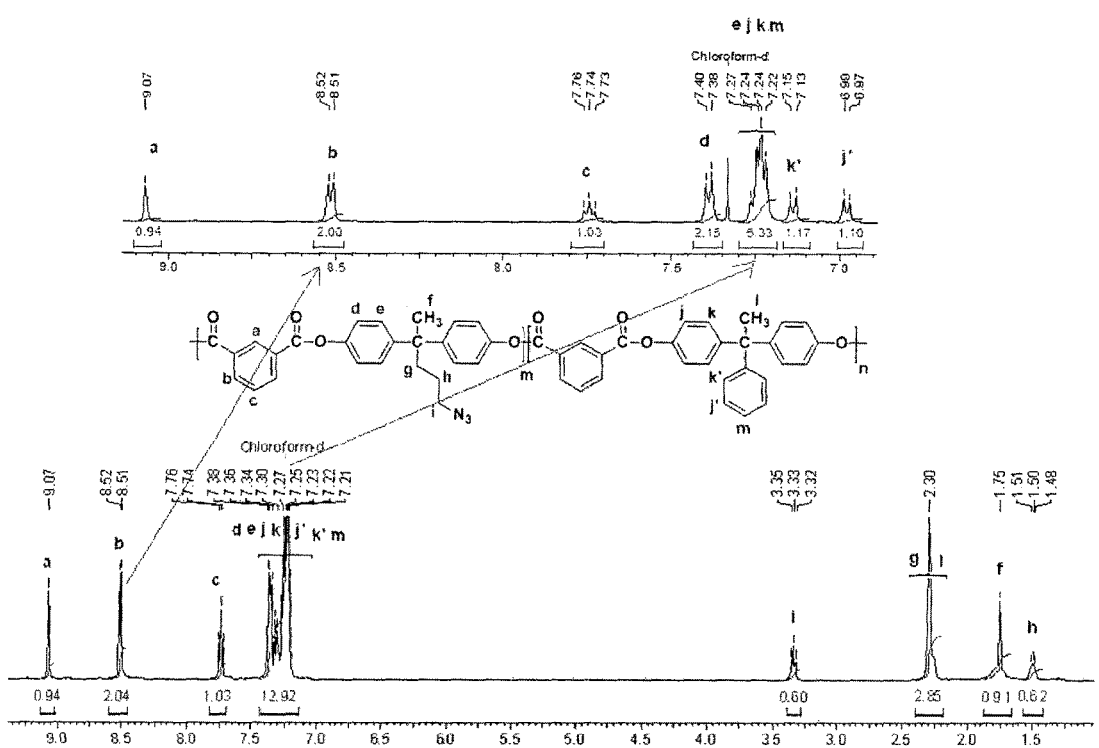
FIG. 2 illustrates $^1$H-NMR spectrum of copolyester obtained by copolycondensation of a mixture of 4,4'-(5-azidopentane-2,2-diyl)diphenol and 4,4'-(1-phenylethane-1,1-diyl)diphenol with isophthaloyl chloride.

Molecular Weight: Mn=85,500 g/mol (GPC in Chloroform, Polystyrene standard) IR-2099 cm$^{-1}$ NMR—$^1$H-NMR spectrum of copolyester of 4,4'-(5-azidopentane-2,2-diyl)diphenol and 4,4'-(1-phenylethane-1,1-diyl)diphenol with isophthaloyl chloride is shown in FIG. 2.

Example 6

Click Reaction of Azido Functionalized Polyester with Phenyl Acetylene

Into a Schlenk tube equipped with a magnetic stirring bar were placed copolyester of 4,4'-(5-azidopentane-2,2-diyl) diphenol and 4,4'-(1-phenylethane-1,1-diyl)diphenol with isophthaloyl chloride (0.20 g, 2.23×10-3 mmol), phenyl acetylene (0.0059 g, 5.7×10-2), N,N,N',N'',N''-pentamethyldiethylenetriamine (0.0034 g, 1.81×10-4 mol), CuBr (0.0027 g, 1.88×10-4 mol) and dimethylformamide (10 mL). The tube was degassed by three freeze-pump-thaw cycles and sealed under nitrogen atmosphere. The reaction mixture was stirred at 50° C. for 24 h. After completion of the reaction time, the reaction mixture was diluted with chloroform (150 mL) and then passed through a column of neutral alumina to remove metal salts. The reaction mixture was concentrated and precipitated into methanol. The filtrate was dried under vacuum at room temperature for 12 h to obtain the modified polyester. The success of click reaction was confirmed by FT-IR spectroscopy. The disappearance of the absorption peak at 2093 cm−1 associated with the azido group evidenced the quantitative fictionalization.

Figure 3:
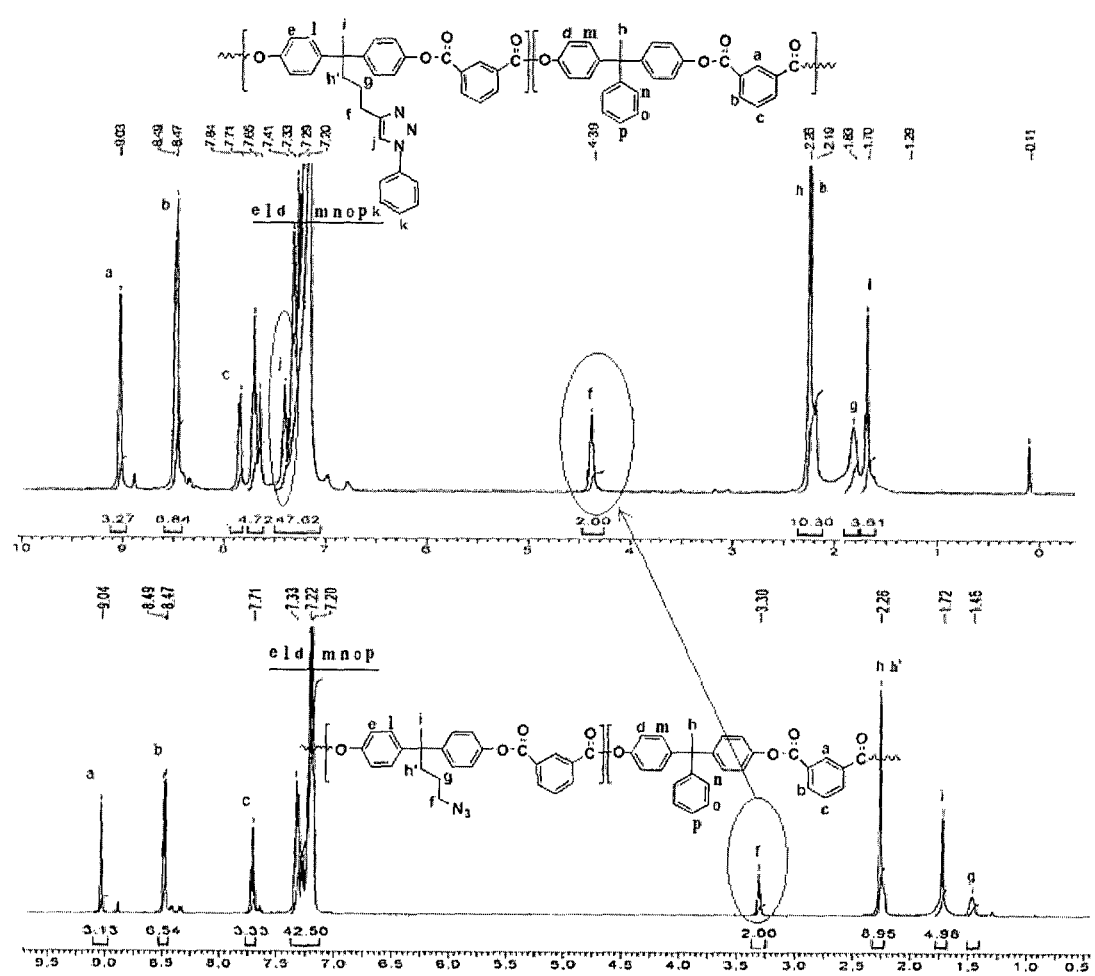
FIG. 3 illustrates $^1$H-NMR spectrum of copolyester after click chemistry modification of polyester based on 4,4'-(5-azidopentane-2,2-diyl)diphenol and 4,4'-(1-phenylethane-1,1-diyl)diphenol with isophthaloyl chloride.

NMR—$^1$H-NMR spectrum of copolyester of 4,4'-(5-azidopentane-2,2-diyl)diphenol and 4,4'-(1-phenylethane-1,1-diyl)diphenol with isophthaloyl chloride after click is shown in FIG. 3.

Example 7

Synthesis of polyester by low temperature solution polymerization of 4,4'-(5-azidopentane-2,2-diyl)diphenol and terephthaloyl chloride Into a 100 mL three-neck round bottom flask equipped with a magnetic stirrer, a nitrogen gas inlet, and CaCl$_2$ guard tube were placed 0.500 g (1.683 mmol) of 4,4'-(5-azidopentane-2,2-diyl)diphenol, 10 mL of DCM, and 0.4 mL of triethylamine, and the solution was cooled to 0° C. To this solution a solution of 0.341 g (1.683 mmol) of terephthaloyl chloride in 5 mL of DCM was added dropwise over a period of 20 min. With the help of additional DCM (3 mL), acid chloride was washed into the reaction flask. The reaction mixture was stirred at 0° C. for 30 min and at 25° C. for 1 h. The viscous solution was diluted with 5 mL of DCM, and the diluted mixture was poured slowly into 50 mL of n-hexane to precipitate the white polymer. The precipitated polymer was isolated by filtration, washed with water (6*100 mL), and dried at 50° C./1 mmHg for 20 h.

ADVANTAGES OF THE INVENTION

Bisphenols containing azido groups are versatile and useful monomers for preparation of high performance polymer containing pendent reactive groups. Azido groups are known to undergo click reaction with alkynes in a facile manner and also could be conveniently transformed into amino groups by reduction reaction. Furthermore, azido groups provide reactive sites for cross-linking under photochemical conditions, thus providing an opportunity for converting thermoplastics into thermosettings.

We claim:

1. Novel bis(4-hydroxyphenyl)alkyl azide compounds of Formula I,

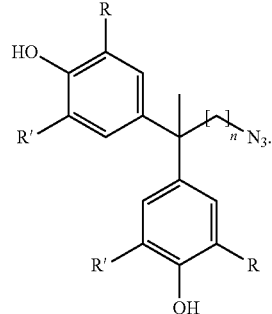

Formula I

Bis(4-hydroxyphenyl) alkyl azides

R and R' = —H, alkyl (linear or branched), —Cl, —Br, NO$_2$ $n$ = 1-36

2. The bis(4-hydroxyphenyl)alkyl azide compounds of Formula I as claimed in claim 1, wherein said compound is 4,4'-(5-azidoalkane-2,2-diyl)diphenol for formula II

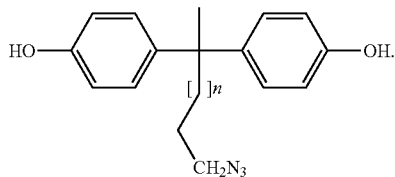

Formula II

3. The bis(4-hydroxyphenyl)alkyl azide compounds of Formula I as claimed in claim 1, wherein said compound is 4,4'-(5-azidopentane-2,2-diyl)diphenol for formula III

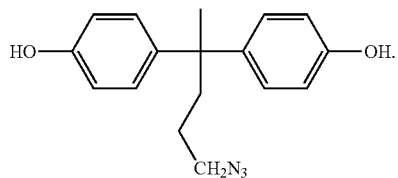

Formula III

4. A process for the synthesis of polyesters or copolyesters of the compound of formula I as claimed in claim 1, wherein said process is selected from interfacial polycondensation and solution polycondensation.

5. The process as claimed in claim 4, wherein said interfacial polycondensation process comprises:
   a. dissolving 4,4'-(5-azidoalkane-2,2-diyl)diphenol in an alkali solution and stirring the mixture to obtain the reaction mixture;
   b. adding benzyl triethyl ammonium chloride to the reaction mixture of step (a) and stirring followed by addition of a solution of diacid chloride in dichloromethane to the reaction mixture and stirring vigorously;
   c. pouring the reaction mixture of step (b) into hot water; filtering the precipitated polymer and washing it several times with water followed by work-up to obtain the desired product.

6. The process as claimed in claim 5, wherein said diacid chloride is selected from terephthaloyl chloride, isophthaloyl chloride and mixtures thereof.

7. The process as claimed in claim 4, wherein said solution polycondensation process comprises:
   a. cooling a solution of 4,4'-(5-azidopentane-2,2-diyl) diphenol to 0° C.;
   b. adding a solution of diacid chloride drop wise with stirring to obtain a solution and
   c. pouring the solution of step b into hexane to obtain the desired product.

8. The process as claimed in claim 7, wherein said diacid chloride is selected from terephthaloyl chloride, isophthaloyl chloride and mixtures thereof.

9. The modified polymers or graft copolymers prepared using the compound of Formula I as claimed in claim 1.

10. A process for preparing the bis(4-hydroxyphenyl)alkyl azide compound of Formula I and more particularly 4,4'-(5-azidoalkane-2,2-diyl)diphenol of Formula II, said process comprising the steps of:
    a) esterification of 4,4'-bis(4-hydroxyphenyl)alkanoic acid using methanol in the presence of concentrated sulphuric acid catalyst and purifying product of reaction to obtain alkyl 4,4'-bis(4-hydroxyphenyl)alkanoate;
    b) reduction of alkyl 4,4'-bis(4-hydroxyphenyl)alkanoate of step (a) using lithium aluminium hydride to obtain 4,4'-(5-hydroxyalkane-2,2-diyl)diphenol;
    c) bromination of 4,4'-(5-hydroxyalkane-2,2-diyl)diphenol of step (b) using carbon tertabromide and triphenyl phosphine to obtain 4,4'-(5-bromoalkane-2,2-diyl)diphenol; and
    d) substitution of bromo group in 4,4'-(5-bromoalkane-2,2-diyl)diphenol of step (c) using sodium azide in a solvent to obtain 4,4'-(5-azidoalkane-2,2-diyl)diphenol.

11. The process as claimed in claim 10, wherein the solvent in said process is selected from DMSO, DMF, DMAc and acetonitrile.

12. A process for the synthesis of modified polymers or graft copolymers from the polymer synthesized from the compound of Formula I as claimed in claim 1 by reacting with alkynes, substituted alkynes or polymers terminated with alkynes, said process comprising: reacting the polymers based on the compound of Formula I with alkynes, substituted alkynes or polymers terminated with alkynes in a sealed, inert atmosphere and working up to obtain the desired product.

* * * * *